Jan. 20, 1948. M. DENOYEL Plant Pat. 781
ROSE PLANT
Filed Nov. 4, 1942
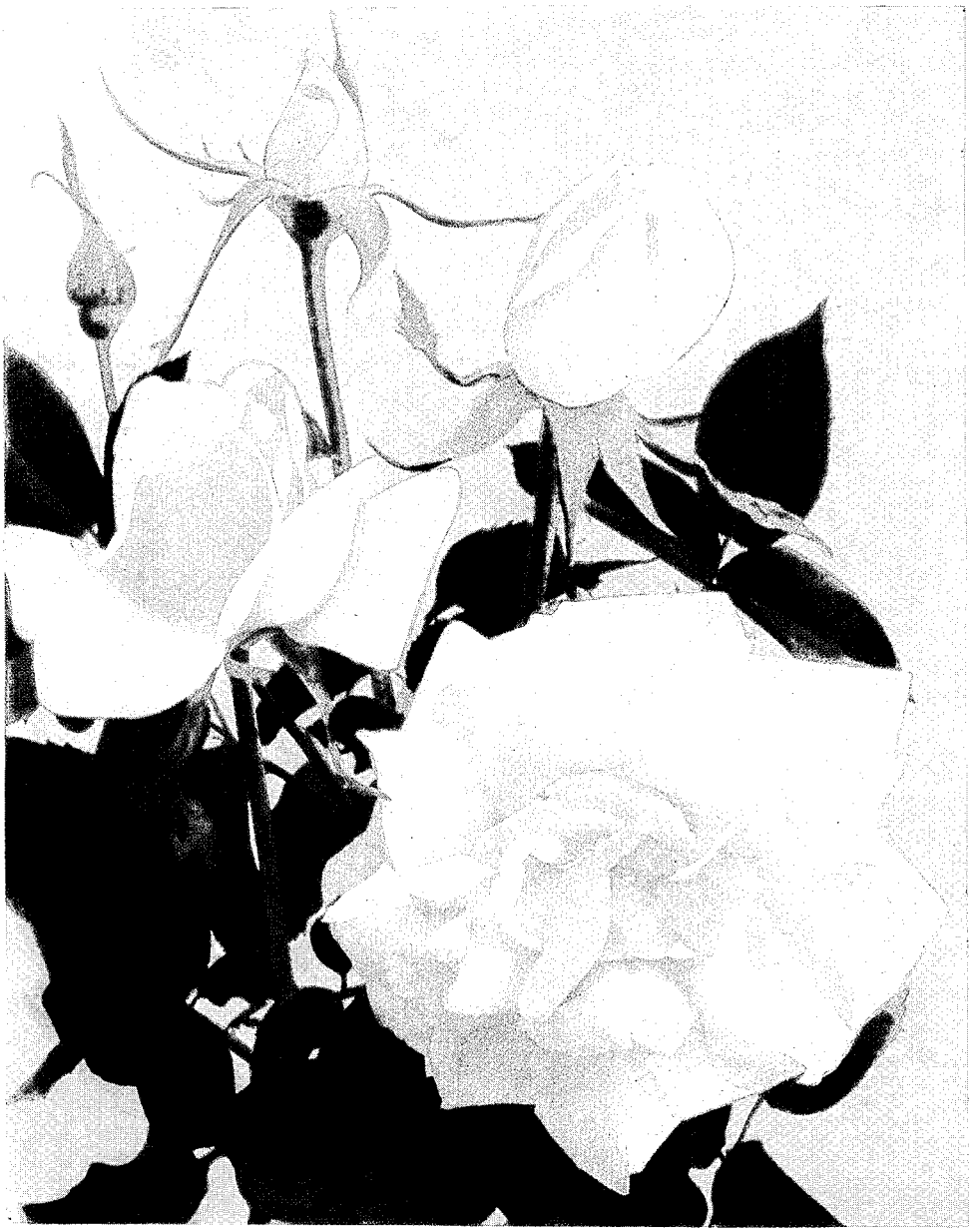
Inventor
Marguerite Denoyel
By Robert Robb
Attorneys Patented Jan. 20, 1948

UNITED STATES PATENT OFFICE

781

ROSE PLANT

Marguerite Dénoyel, Venissieux, Lyon, France, assignor to Jackson & Perkins Company, Newark, N. Y., a corporation of New York Application November 4, 1942, Serial No. 464,556

1 Claim. (Cl. 47—61)

The present invention relates to a new and distinct variety of rose plant, the result of a definite effort to produce a rose representing an improvement upon the parents and in class of hybrid teas.

This new variety is characterized as to novelty by its habit of upright growth, the abundance of its leathery Yew Green foliage closely spaced on the stems, and the large individual flowers of Begonia Pink which on ageing uniformly lightens to Rose Doree, giving always the impression of rich pink, quite unusual in pink roses due to the underlying Lemon Chrome coloring which permeates each petal.

The following is a detailed description of the new variety, color terminology being in accord with Ridgway's Color Standard:

Parentage: Seedling.
*Seed parent.*—Unnamed seedling.
*Pollen parent.*—Unnamed seedling.
Classification: Botanic and commercial—hybrid tea.

*Flower*

(Observations made in the afternoon of September 22, 1941, at Newark, New York.)

Blooming habit: Recurrent—continuous.
Bud:
*Size.*—Large.
*Form.*—Pointed. Is not affected by wet or hot weather.
*Color.*—When sepals first divide—Carmine, Plate 1. When petals begin to unfurl—Scarlet Red, Plate 1. When half blown—Inside of petals, Begonia Rose, Plate 1; reverse of petals, Eosine Pink, Plate 1.
*Sepals.*—Branched, "hood" above bud. Curl back when petals begin to unfurl. Color—outside, Yellowish Oil Green, Plate 5; inside, Pale Cendre Green, Plate 6.
*Calyx.*—Shape—apple. Size—broad. Aspect — smooth. Color — Lettuce Green, Plate 5.
*Peduncle.*—Aspect—smooth. Color—Yellowish Oil Green, Plate 5. Strength—erect; slender.
*Opening.*—Bud opens well. Is not affected by adverse conditions.
Bloom:
*Size.*—Large. Average size when fully expanded, four inches.
*Borne.*—Singly.
*Stems.*—Medium length; strong.
*Form.*—When first open—high center. Permanence—retains its form to the end.

*Petalage.*—Double (full but open center). Number of petals under normal conditions, 35.
*Color.*—Center of flower—Begonia Rose, Plate 1. Outer petals—Rose Doree, Plate 1. Base of petals (aiglet)—Lemon Chrome, Plate 4. Inside of petals—Begonia Rose, Plate 1, with slight overcast of Lemon Chrome, Plate 4, extending over the lower half of the petal. Reverse of petals—Geranium Pink, Plate 2, with slight veining of Martius Yellow, Plate 4. General tonality from a distance—Rose Doree, Plate 1.
*Discoloration.*—General tonality at end of first day—Begonia Rose, Plate 1. Second day—Rose Doree, Plate 1. Third day—Geranium Pink, Plate 2.
Petals:
*Texture.*—Leathery. Is not affected by wet or hot weather.
*Appearance.* — Inside — satiny. Outside — shiny.
*Form.*—Oval.
*Arrangement.*—Irregular. Petaloids in center—few; small.
*Persistence.*—Drop off cleanly.
*Fragrance.*—Slight. Nature—Tea (average hybrid tea scent).
*Lasting quality.*—On the plant and as cut flower—long.
Genital Organs:
*Stamens, anthers.*—Large; many. Color—Light Cadmium, Plate 4. Arrangement—regular around styles.
*Stamens, filaments (threads).*—Long. Color—Lemon Chrome, Plate 4.
*Pollen.*—Lemon Yellow, Plate 4.
*Styles.*—Bunched, uneven length; medium length, heavy.
*Stigmas.*—Pinard Yellow, Plate 4.
*Ovaries.*—All enclosed in calyx.

*Plant*

Form: Bush.
Growth: Vigorous; branching.
Foliage: 5 leaflets.
*Size.*—Medium.
*Quantity.*—Normal.
*Color.*—New foliage: upper side—Yellowish Oil Green, Plate 5; under side—Light Cress Green, Plate 31. Old foliage: upper side—Yew Green, Plate 31; under side—Rainette Green, Plate 31.
*Shape.*—Oval pointed.
*Texture.* — Upper side — leathery; under side—rough. Ribs and veins—ordinary.

*Edge.*—Serrated (saw toothed).

*Serrations.*—Single; small.

*Rachis.*—Color—Rainette Green, Plate 31. Under side—Prickles.

*Stipules.*—Medium length; smooth.

*Disease resistance.*—Resistant, as determined by observation of the plant during its development in association with other varieties grown under comparable conditions.

Wood:

*New wood.* — Color — Oil Green, Plate 5. Bark—smooth.

*Old wood.*—Color—Cress Green, Plate 31. Bark—smooth.

Thorns:

*Thorns.*—Quantity—on main stalks from base—ordinary. On laterals from stalk—few. Form—narrow; short; hooked downward. Color when young—Kaiser Brown, Plate 14. Position—irregular.

*Prickles.*—Quantity—on main stalks and on laterals—none.

*Short needles.*—Quantity—on main stalks and on laterals—none.

I claim:

A new and distinct variety of rose plant, characterized as to novelty by its habit of rugged upright growth, the color and abundance of its leathery foliage closely spaced on the stems, and the large size and color of the individual flowers which tend to uniformly lighten from Begonia Pink to Rose Doree in a manner unusual among pink roses, substantially as shown and described.

MARGUERITE DÉNOYEL.